United States Patent [19]

Melloh et al.

[11] 4,307,089

[45] Dec. 22, 1981

[54] COMPOSITIONS OF PYRITHIONE METAL SALTS AND UNDECYLENIC ACID ALKYLOLAMIDE DERIVATIVES

[75] Inventors: Wilhelm Melloh, Bad Soden bei Salmunster; Robert Tanck, Düsseldorf, both of Fed. Rep. of Germany

[73] Assignee: Rewo Chemische Werke GmbH, Steinau an der Strasse, Fed. Rep. of Germany

[21] Appl. No.: 173,588

[22] Filed: Jul. 30, 1980

[30] Foreign Application Priority Data

Aug. 2, 1979 [DE] Fed. Rep. of Germany ....... 2931379

[51] Int. Cl.³ .............................................. A61K 31/555
[52] U.S. Cl. ...................................... 424/245; 252/106; 252/107; 260/404; 260/404.8; 424/DIG. 4; 424/65; 424/308; 424/359
[58] Field of Search ................... 424/245, 70, DIG. 4, 424/65

[56] References Cited

U.S. PATENT DOCUMENTS

| | | | |
|---|---|---|---|
| 3,236,733 | 2/1966 | Karsten et al. | 424/DIG. 4 |
| 3,385,755 | 5/1968 | Seebohm | 424/308 |
| 3,862,305 | 1/1975 | Bouillon et al. | 424/DIG. 4 |
| 3,950,532 | 4/1976 | Bouillon et al. | 424/DIG. 4 |
| 3,961,054 | 6/1976 | Furia et al. | 424/DIG. 4 |

OTHER PUBLICATIONS

Lubowe, Journ. of the Soc. of Cosm. Chemists, 6/1961, vol. 12, No. 5, pp. 253-258.
Brauer et al., The Journal of Invest. Derm., 1966, vol. 47, No. 2, pp. 174 & 175.
Kalish, Drug & Cosm. Industry, 8/1967, p. 153.

*Primary Examiner*—Dale R. Ore
*Attorney, Agent, or Firm*—Curtis, Morris & Safford

[57] ABSTRACT

Antimicrobial compositions useful in the preparation of cosmetic formulations, including preparations effective for the treatment of dandruff, are provided. The antimicrobial compositions of the invention consist of a pyrithione compound in combination with an undecylenic acid monoalkylolamide sulfosuccinate half ester.

10 Claims, No Drawings

COMPOSITIONS OF PYRITHIONE METAL SALTS AND UNDECYLENIC ACID ALKYLOLAMIDE DERIVATIVES

BACKGROUND OF THE INVENTION

U.S. Pat. No. 3,385,755 discloses antibacterial and antifungal agents derived from undecylenic acid alkylolamides. The derivatives are water soluble and are suitable for use in a variety of useful compositions, including compositions for the treatment of dandruff. One such useful derivative is the undecylenic monoalkylolamide sulfosuccinate half ester of the formula

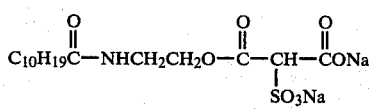

Salts of the undecylenic monoalkylolamide sulfosuccinate esters are also employed in combination with 3-trifluoromethyl-4,4'-dichlorocarboanilide or 3,4,4'-trichlorocarboanilide to provide shampoo formulations effective against microorganisms normally associated with the presence of dandruff (see Japanese appln. No. SHO-42-83663 published Aug. 24, 1971).

In U.S. Pat. No. 3,236,733 a method of combatting dandruff is described using pyridinethione metal salts (e.g. zinc pyridinethione) detergent compositions. German appln. No. 22 62 375 also shows the use of soluble combinations of zinc and zirconium pyrithiones to provide effective antidandruff treatment.

While the metal salts and other derivatives of 1-hydroxy-2-pyridinethione and its tautomeric form 2-pyridinethiol-1-oxide (or 2-mercaptopyridine-N-oxide) are known to be effective bacteriocides and fungicides for use in medicated shampoos for the treatment and control of dandruff, the toxicity of these compounds is relatively high and, in many instances, they are extremely irritating to the skin and eyes. The reported 24-hour acute oral lethal dosis ($LD_{50}$) of zinc pyrithione is 300 mg/kg in mice and 200 mg/kg in male rats. The 24 hour acute $LD_{50}$ of sodium pyrithione is approximately 1100 mg/kg in rats. A 40% solution of the sodium pyrithione does not irritate rabbit eyes but does irritate the skin. A 48% dispersion of the zinc pyrithione irritates the skin and is extremely irritating to the eyes of rabbits.

SUMMARY OF THE INVENTION

We have now quite unexpectedly discovered that combinations of undecylenic acid alkylolamide derivatives with pyrithione metal salts are extremely effective antimicrobial compositions. The compositions of this invention can be employed in combination with other known ingredients for the formulation of highly useful cosmetic preparations and are particularly useful in the formation of shampoos for the treatment of dandruff.

These compositions are advantageous in that they exhibit antiseborrheic, antibacterial and antifungal properties and are particularly effective against organisms typically associated with the presence and formation of dandruff. They are further advantageous in that a high degree of efficacy is achieved using significantly reduced levels of the very costly and toxicologically less desirable pyrithione metal salt. With the compositions of the present invention it is therefore readily possible to provide highly effective cosmetic formulations, particularly antiseborrheic and antidandruff shampoo formulations, employing a minor proportion of the pyrithione metal salt (e.g. zinc pyrithione) and a major proportion of the economically and toxicologically more desirable undecylenic acid alkoylolamide derivative. In still another even more desirable aspect of the invention, synergistic antibacterial compositions for combatting dandruff may be obtained.

Compositions of this invention are comprised of 50 to 95 wt. percent undecylenic alkylolamide sulfosuccinate half ester compound and 5 to 50 wt. percent of the pyrithione metal salt or similarly effective pyrithione compound. Especially useful compositions contain 80 to 90% by weight undecylenic alkylolamide sulfosuccinate half ester and 10 to 20% by weight pyrithione metal salt. The above compositions are formulated with other known cosmetic ingredients to obtain useful toiletry products and especially antidandruff hair cleaning preparations.

DETAILED DESCRIPTION

By means of this invention it is now possible to offer cosmetic formulations containing only a minor percentage of pyrithione compound without detracting from the overall antibacterial, antifungal, antiseborrheic and antidandruff properties. Furthermore, economic and toxicological advantages are realized by reducing the amount of the pyrithione compound used. To achieve these and other desirable results, an undecylenic acid alkylolamide derivative is employed in conjunction with the pyrithione compound.

To obtain the improved compositions of this invention an undecylenic alkylolamide sulfosuccinic half ester is employed. The sulfosuccinate half esters will correspond to the formula

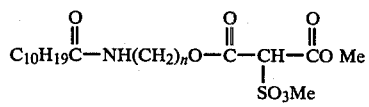

where n is 2 or 3 and Me represents a metal, preferably sodium. Such compounds are known and di-sodium undecylenic acid ethanolamide sulfosuccinate is commercially available as a powder or 50% solution from Emery Industries, Inc. as Rewocide ® SBU 185. Sulfosuccinate half esters are obtained from the reaction of succinic anhydride with undecylenic acid monoethanolamide or undecylenic acid monoisopropanolamide in accordance with the teachings of U.S. Pat. No. 3,385,755.

The above-described undecylenic monoalkylolamide sulfosuccinate half ester is combined with a pyrithione metal salt or similarly effective pyrithione derivative. Useful pyrithione (pyridinethione) derivatives are derivatives of 1-hydroxy-2-pyridinethione or tautomeric form thereof. Various pyrithione metal salts and derivatives are known and described in numerous references such as in U.S. Pat. Nos. 2,809,971, 2,742,476 and 3,236,733. Heavy metal salts and dimeric forms of pyrithione are useful for the preparation of the compositions of this invention. The zinc and sodium salts of pyrithione and compounds having two pyrithione moieties linked via a disulfide bridge, such as 2,2'-dithiobis(pyridine-1-oxide) or the magnesium sulfate adduct thereof, are most generally used and provide extremely effective antibacterial compositions.

The compositions of this invention contain 50% to 95% by weight undecylenic monoalkylolamide sulfosuccinate half ester and 5% to 50% by weight of the pyrithione derivative. Particularly useful compositions contain 80 to 90 wt. % of the undecylenic acid derivative and 10 to 20 wt. % pyridinethione compound.

In view of the reduced amount of the pyrithione compound which can be employed, a significant economic advantage can be realized and the compositions and the resulting formulations prepared therefrom are toxicologically more desirable. Furthermore, in some instances synergistic combinations may result so that it is possible to obtain products which exhibit enhanced antibacterial activity. While it is highly desirable, based on economic considerations alone, to replace the pyrithione component with less costly material, there is also a movement by regulatory bodies, based on toxicological considerations, to limit the effective amount of pyrithione derivatives in cosmetic formulations. As a result of this invention it is now possible to prepare effective cosmetic formulations which satisfy, for example, the requirements of the Europarat, a public body which in study published in 1978 recommended that the concentration of sodium pyrithione, for instance, be limited to a level of 0.5%. Reduction of the concentration of zinc pyrithione to a maximum level of 1%, calculated as zinc, has also been recommended by the "Kosmetikverordnung" as published on Dec. 16, 1977 on behalf of the "Deutsche Bundesgesundheitsamt". By utilizing the undecylenic acid alkylolamide sulfosuccinate half ester, which is essentially completely non-toxic (oral $LD_{50}$ for mice greater than 10,000 mg/kg body weight), it is possible to effectively reduce the amount of pyrithione derivative to the levels recommended by the aforementioned agencies and thereby improve the overall toxicological properties of the resulting cosmetic formulations without detracting from their desirable characteristics.

The ratio of undecylenic monoalkylolamide derivative to pyrithione compound and the amount of the composition used will vary depending on the particular formulation and the desired end-use application. Typically, however, the compositions of this invention (i.e. the combined undecylenic acid and pyrithione components) comprise no more than 10% by weight of the total cosmetic formulation. For antidandruff shampoo preparations, about 2% to 6% of the composition will generally be used. In other liquid hair care preparations, the combinations of this invention will generally be present at a 1 to 5 wt. % level. The compositions will generally comprise from about 2 to 6% by weight of deodorizing preparations.

The present compositions are compatible with other widely used cosmetic ingredients and they can be formulated with varying proportions of these ingredients to provide a wide variety of useful preparations. Typical cosmetic ingredients with which the combinations of this invention can be used include anionic, nonionic or amphoteric surfactants or mixtures thereof, superfatting agents, plant extracts, essential oils and perfumes, colorants, preservations and the like. Conventional materials such as fatty acid alkylolamides, protein hydrolysates and lanolin or its derivatives can be employed for the purpose of superfatting.

An exemplary hair cleansing preparation, based on anionic surfactants, consists of the following:

| INGREDIENTS | PARTS |
|---|---|
| Sodium laurylethersulfate (28%) | 50 |
| Sodium laurylsulfate (28%) | 10 |
| Stearic acid monoglyceride | 4 |
| Coconut fatty acid diethanolamide | 2 |
| Sodium chloride | 2 |
| Water, Perfume, Colour, Perservatives | ad 100 |

To demonstrate the ability of the compositions of this invention to be utilized in antidandruff shampoo formulations and to demonstrate the improved results obtained thereby, two shampoo formulations were prepared in accordance with the above recipe and evaluated clinically for the treatment of dandruff. The first formulation (Shampoo No. 1) contained 1% by wt. zinc pyrithione as the active antidandruff agent and the second formulation (Shampoo No. 2) contained 0.4 wt. percent zinc pyrithione and 2.5 wt. percent di-sodium undecylenic acid ethanolamide sulfosuccinate.

For the clinical evaluation 100 subjects suffering from dandruff were chosen—50 subjects (Group A) used Shampoo No. 1 and 50 subjects (Group B) used Shampoo No. 2. After three weeks use, scalps of the persons completing the test were examined and the results are recorded in the table below. A second three week evaluation was conducted except that for this test Group A used Shampoo No. 2 and Group B used Shampoo No. 1. Results of this clinical trial are also set forth in the table. Numbers in the table are the number of persons with the indicated result.

| | GROUP A SHAMPOO No. 1 | GROUP B SHAMPOO NO. 2 | GROUP B SHAMPOO NO. 1 | GROUP A SHAMPOO NO. 2 |
|---|---|---|---|---|
| Well above average improvement | 3 | 4 | 7 | 26 |
| Less dandruff | 26 | 23 | 4 | 6 |
| Somewhat less dandruff | 6 | 9 | 1 | 6 |
| No effect | 13 | 11 | 30 | 9 |
| Worse than before | 2 | 0 | 5 | 0 |

It is evident from the data obtained from the clinical study and presented above that the formulation (Shampoo No. 2) prepared in accordance with this invention, i.e. using a combination of di-sodium undecylenic acid monoethanolamide sulfosuccinate and zinc pyrithione, exhibits better scale-supressing effect than the shampoo formulation prepared using a higher concentration of the zinc pyrithione, by itself. It is also clearly shown that it is now possible with this invention to obtain effective dandruff control with shampoo formulations containing only 0.4 wt. percent zinc pyrithione.

The following formulations serve to further illustrate various cosmetic preparations which can be obtained utilizing the compositions of this invention. All parts and percentages are given on a weight basis unless indicated otherwise.

An antidandruff shampoo, based on anionic surfactants, was prepared in accordance with the following recipe:

| INGREDIENTS | PARTS |
|---|---|
| Disodium fatty alcohol polyglycolether | |

| INGREDIENTS | PARTS |
|---|---|
| sulfosuccinate (40% aqueous solution) | 20.0 |
| Triethanolammonium lauryl sulfate (30% aqueous solution) | 30.0 |
| Zinc pyrithione | 0.8 |
| Disodium undecylenic acid monoethanolamine sulfosuccinate half ester (50% aqueous solution) | 5.0 |
| Polyethylene glycol distearate | 2.0 |
| Coco fatty acid diethanolamide | 3.0 |
| Glycol distearate | 1.5 |
| Citronellic acid | 0.5 |
| Ammonium chloride | 2.5 |
| Water | 35.0 |

For the preparation of the shampoo formulation the ingredients were combined and mixed in a vessel while stirring and heating to 60° C. to 70° C. A homogeneous mixture was obtained which upon cooling had a stable pearly luster.

Another hair shampoo prepared using amphoteric surfactants and exhibiting good substantivity was prepared in accordance with the following formulation:

| INGREDIENTS | PARTS |
|---|---|
| N-β-hydroxyethyl-N-carboxymethyl fatty amidoethyl amine (50% in water) | 25.0 |
| Triethanol ammonium laurysulfate (40% in water) | 20.0 |
| Disodium undecylenic acid monoethanolamide sulfosuccinate (50% solution) | 6.0 |
| Zinc pyrithione | 0.5 |
| Magnesium-aluminum silicate | 3.5 |
| Linoleic acid ethanolamide | 2.0 |
| Water, Perfume, Dye, Preservative | 43.0 |

The preparation of this shampoo involves intensive mixing at 50° C. to 60° C. The magnesium-aluminum silicate serves to solubilize the zinc pyrithione which by itself is not water soluble.

A shampoo exhibiting antiscaling characteristics was prepared as follows:

| INGREDIENT | PARTS |
|---|---|
| Isopropyl alcohol | 40.0 |
| n-Propyl alcohol | 10.0 |
| Undecylenic acid diethanolamide | 5.0 |
| Disodium undecylenic acid monoethanolamide sulfosuccinate (50% solution) | 2.0 |
| Sodium pyrithione | 0.2 |
| Glycerine | 4.0 |
| Diisopropyl adipate | 2.0 |
| Perfume Oil | 0.8 |
| Water | 36.0 |

To prepare the formulation, the water-soluble and alcohol-soluble components were first mixed and were than combined at room temperature to produce a clear solution.

A deoderant cream was prepared as follows:

| INGREDIENT | PARTS |
|---|---|
| Stearic acid | 12.0 |
| Cetyl alcohol | 5.0 |
| Stearic acid polyglycol ester | 6.0 |
| Sorbitan solution (50% in water) | 13.0 |
| Disodium undecylenic acid monoethanolamide sulfosuccinate (50% solution) | 6.0 |
| 2,2'-dithiobis(pyridine-1-oxide) | 0.2 |
| Water, Perfume, Preservative | 57.8 |

The preparation was made by combining and mixing the ingredients at 75° C. in a homogenizer and slowly cooling to room temperature.

In addition to being useful in formulations such as those prepared above, in view of their high antimicrobial activity the compositions of this invention can be used in the preparation of other personal care products such as soap bars, surgical scrubs, topical ointments or powders for the treatment of athletes foot and acne and in the preparation of numerous sanitizing formulations. The compositions of this invention are effective antimicrobial agents for a broad range of organisms including gram positive bacteria, gram negative bacteria, molds and yeasts such as, for example:

bacillus subtilis;
micrococcus agilis;
staphylococcus epidermis;
staphylococcus aureus;
streptococcus faecalis;
escherichia coli;
klebsiella pneumoniae;
proteus vulgaris;
pseudomonas glycinea;
salmonella typhimurium;
xanthomonas cucurbitae;
aspergillus niger;
aspergillus oryzae;
cephalosporium acremonium;
helminthosporium populosum;
phytophthora infestans;
pityrosporum ovale;
candida albicans;
saccharomyces cerevisiae; and the like.

We claim:

1. An antibactericidal and antifungicidal composition consisting essentially of 50% to 95%, by weight, undecylenic acid monoalkylolamine sulfosuccinate half ester of the formula

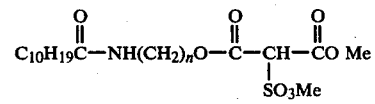

wherein n is 2 to 3 and Me represents a metal and 5% to 50%, by weight, pyrithione compound selected from the group consisting of sodium pyrithione, zinc pyrithione, 2,2'-dithiobis(pyridine-1-oxide) or the magnesium sulfate adduct of 2,2'-dithiobis(pyridine-1-oxide).

2. The composition of claim 1 wherein the metal Me of the undecylenic acid monoalkylolamide sulfosuccinate half ester is sodium.

3. The composition of claim 2 containing 80% to 90%, by weight, of the undecylenic acid monoalkylolamide sulfosuccinate half ester and 10% to 20%, by weight, of the pyrithione compound.

4. An antidandruff preparation containing up to 10%, by weight based on the total formulation, of an antibactericidal and antifungicidal composition consisting of 50% to 95%, by weight, undecylenic acid monoalkylolamide sulfosuccinate half ester of the formula

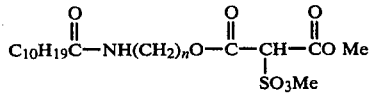

wherein n is 2 to 3 and Me represents a metal and 5% to 50%, by weight, pyrithione compound selected from the group consisting of sodium pyrithione, zinc pyrithione, 2,2'-dithiobis(pyridine-1-oxide) or the magnesium sulfate adduct of 2,2'-dithiobis(pyridine-1-oxide).

5. The antidandruff preparation of claim 4 which is a water-based shampoo formulated using anionic surfactants.

6. The antidandruff preparation of claim 4 which is a water-based shampoo formulated using nonionic surfactants.

7. The antidandruff preparation of claim 4 which is a water-based shampoo formulated using amphoteric surfactants.

8. The antidandruff preparation of claim 5, 6 or 7 wherein the antibactericidal and antifungicidal composition consists of 80% to 90%, by weight, undecylenic acid monoalkyolamide sulfosuccinate half ester and 10% to 20%, by weight, pyrithione compound.

9. The antidandruff preparation of claim 8 containing 0.5 weight percent or less of the pyrithione compound, based on the total formulation.

10. A method of imparting antibactericidal and antifungicidal activity to a cosmetic formulation by incorporating therein an effective amount of a composition consisting of 50% to 95%, by weight, undecylenic acid monoalkylolamide sulfosuccinate half ester of the formula

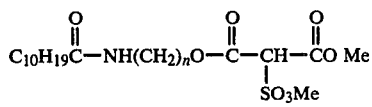

wherein n is 2 to 3 and Me represents a metal and 5% to 50%, by weight, pyrithione compound selected from the group consisting of sodium pyrithione, zinc pyrithione, 2,2'-dithiobis(pyridine-1-oxide) or the magnesium sulfate adduct of 2,2'-dithiobis(pyridine-1-oxide).

* * * * *